United States Patent

Coudert et al.

[11] Patent Number: 5,807,882
[45] Date of Patent: Sep. 15, 1998

[54] ANTHRACENE COMPOUNDS USEFUL IN TREATING CERTAIN CANCERS

[75] Inventors: Gérard Coudert, Saint Denis en Val; Siham Khatib, Orleans; Pascale Moreau, Clermont Ferrand; Daniel-Henri Caignard, Le Pecq; Pierre Renard, Versailles; Ghanem Atassi, Saint Cloud; Alain Pierre, Les Alluets le Roi, all of France

[73] Assignee: Adir et Compagnie, Courbevoie, France

[21] Appl. No.: 966,286

[22] Filed: Nov. 7, 1997

[30] Foreign Application Priority Data

Nov. 8, 1996 [FR] France .................. 96 13653

[51] Int. Cl.⁶ .................. A61K 31/40; A61K 31/44; A61K 31/335; C07D 209/56
[52] U.S. Cl. .................. 514/410; 514/280; 514/287; 514/452; 546/48; 546/64; 546/65; 548/418; 549/358
[58] Field of Search .................. 514/410, 280, 514/287, 452; 546/48, 64, 65; 548/418; 549/358

[56] References Cited

PUBLICATIONS

Kamps et al, Cancer Letters, vol. 34, No. 2, pp. 129–137, Feb. 1987.

*Primary Examiner*—William R. A. Jarvis
*Attorney, Agent, or Firm*—The Firm of Gordon W. Hueschen

[57] ABSTRACT

A compound of formula (I):

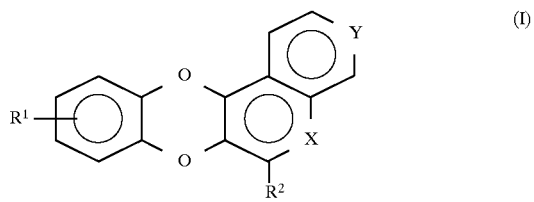

in which $R^1$, $R^2$, X and Y are as defined in the description, the isomers thereof and the addition salts thereof with a pharmaceutically acceptable acid or base, and medicinal products containing the same are useful in the treatment of certain cancers.

10 Claims, No Drawings

ANTHRACENE COMPOUNDS USEFUL IN TREATING CERTAIN CANCERS

FIELD OF THE INVENTION

The present invention relates to new substituted 7,12-dioxabenz[a]anthracene compounds. The compounds of the present invention find advantageous therapeutic use as a result of their antitumor activity.

DESCRIPTION OF THE PRIOR ART

In the literature, the compound 7,12-dioxa-9,10-dichlorobenz[a]anthracene (Biochem. Pharmacol., 1990, 40 (4), pp. 737–741), which interacts with the Ah (aromatic hydrocarbon) receptor of human placenta, is described. However, no therapeutic activity was reported for this compound.

The novelty of the compounds of the present invention lies both in their structure and in their use as antitumor agents.

DETAIL DESCRIPTION OF THE INVENTION

More specifically, the present invention relates to the compounds of formula (I):

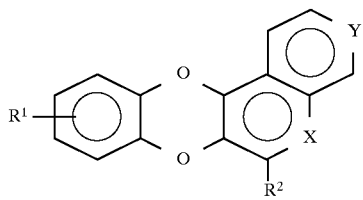

in which:

$R^1$ represents a hydrogen atom or a group of formula O—R, in which R represents a hydrogen atom or a linear or branched ($C_1$–$C_6$) alkyl group (optionally substituted with an aryl or heteroaryl group), $R^2$ represents a hydrogen atom, a halogen atom, a hydroxyl group, linear or branched ($C_1$–$C_6$) alkoxy group, formyl group, $CF_3SO_3$ group, cyano group, linear or branched ($C_1$–$C_6$) alkoxycarbonyl or aryloxycarbonyl group, a NR'aR'b group in which R'a represents a ($C_1$–$C_6$) dialkylaminoalkyl group (each alkyl portion consisting, independently of one another, of an identical or different, linear or branched chain containing from 1 to 6 carbon atoms) and R'b represents a hydrogen atom or a linear or branched ($C_1$–$C_6$) alkyl group, or a group BNR"aR"b in which B represents a carbonyl or methylene group, R"a and R"b have the same definition as R'a and R'b, respectively, or R"a represents a linear or branched ($C_1$–$C_6$) alkyl group substituted with at least one hydroxyl group, X represents a nitrogen atom (optionally substituted with a linear or branched ($C_1$–$C_6$) alkyl group designated R'c), or a group C—$R^3$ in which $R^3$ represents a hydrogen atom, a linear or branched ($C_1$–$C_6$) alkoxycarbonyl group or a group BNR"aR"b in which B represents a carbonyl or a methylene group and R"a and R"b have the same definition as above, or $R^2$ and X, when X represents a group C—R3, with the carbon atom which bears them, together form a ring of formula (II):

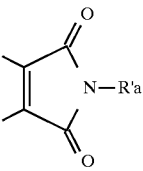

in which R'a has the same definition as above,

Y represents a nitrogen atom or a group C—$R^4$ in which R4 represents a hydrogen atom, or a group of formula O—R" in which R" represents a hydrogen atom, a linear or branched ($C_1$–$C_6$) alkyl group (optionally substituted with a hydroxyl group) or an aryl or heteroaryl group, on the understanding that, when X represents a nitrogen atom and Y a CH group, or when X represents a CH group and Y a nitrogen atom, or when X and Y simultaneously represent a CH group, then $R^1$ and $R^2$ cannot simultaneously represent a hydrogen atom, on the understanding that the term aryl means a phenyl or naphthyl group optionally substituted in an identical or different manner with one or more halogen atoms or linear or branched ($C_1$–$C_6$) alkyl, hydroxyl, linear or branched ($C_1$–$C_6$) alkoxy or trihalomethyl groups, and the term heteroaryl means a mono- or bicyclic aromatic group containing 1 or 2 hetero atoms chosen from O, S and N, optionally substituted in an identical or different manner with one or more halogen atoms or linear or branched ($C_1$–$C_6$) alkyl, hydroxyl, linear or branched ($C_1$–$C_6$) alkoxy or trihalomethyl groups, their isomers as well as their addition salts with a pharmaceutically acceptable acid or base.

Among pharmaceutically acceptable acids, there may be mentioned, with no limitation being implied, hydrochloric, hydrobromic, sulfuric, phosphonic, acetic, trifluoroacetic, lactic, pyruvic, malonic, succinic, glutaric, fumaric, tartaric, maleic, citric, ascorbic, oxalic, methanesulfonic, camphoric, and the like.

Among pharmaceutically acceptable bases, there may be mentioned, with no limitation being implied, sodium hydroxide, potassium hydroxide, triethylamine, tert-butylamine, and the like.

More especially, the present invention relates to:

the compounds of formula (I) in which $R^2$ represents a group NR'aR'b in which R'a represents a (linear or branched ($C_1$–$C_6$) dialkyl)amino(linear or branched ($C_1$–$C_6$)) alkyl group, each alkyl portion being, independently of one another, identical or different, and R'b represents a hydrogen atom or a linear or branched ($C_1$–$C_6$) alkyl group, or the compounds of formula (I) in which $R^2$ or X, when X consists of a group C—$R^3$, represents a group BNR"aR"b in which B is as defined above and R"a and R"b corresponding to R'a and R'b, respectively, are as defined above, or the compounds of formula (I)in which $R^2$ and X, when X represents a group C—$R^3$, form, together with the carbon atom which bears them, a ring of formula (II):

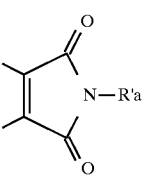

in which R'a has the same meaning as above, and more especially the compounds of formula (I) in which $R^2$ and X, when X represents a group C—$R^3$, form, together with the carbon atom which bears them, a ring of formula (II) in which R' a represents a dimethylaminoethyl group.

The present invention relates more specifically to the compound of formula (I) which is $N^2$-(7,12-dioxa-3-hydroxybenz[a]anthracene-5,6maleimido)-$N^1$,$N^1$-dimethylethylene diamine hydrochloride.

The invention also extends to the process for the preparation of the compounds of formula (I), wherein there is used as starting material:

for the compounds in which X represents a nitrogen atom or a CH group, the compound of formula (III):

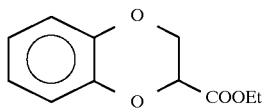

(III)

which is —either brominated and then treated with meta-chloroperbenzoic acid and subjected to the action of potassium iodide to obtain the compound (IIIa):

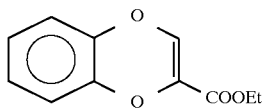

(IIIa)

—or acylated according to a Friedel-Crafts reaction, dibrominated and then treated with meta-chloroperbenzoic acid to yield the compound of formula (IV):

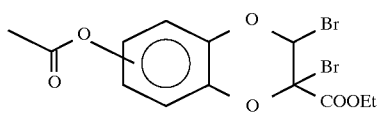

(IV)

which, subjected to the action of sodium iodide and then of a base such as sodium ethylate, enables the compound (V) to be obtained:

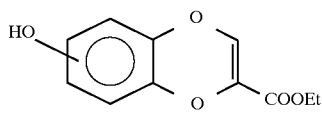

(V)

which is condensed with electrophiles of formula R'''-halogen, in which R''' represents a linear or branched ($C_1$–$C_6$) alkyl group optionally substituted with an aryl or heteroaryl group, to yield the compound of formula (VI):

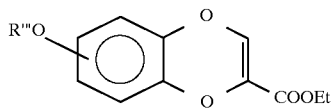

(VI)

in which R''' has the same definition as above, the collective compounds (IIIa) and (VI) forming the compound of formula (VII):

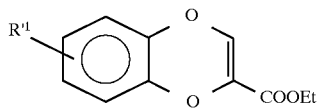

(VII)

in which $R'^1$ represents a hydrogen atom or a linear or branched ($C_1$–$C_6$) alkoxy group optionally substituted with an aryl or heteroaryl group, which is condensed, after saponification, for example with aqueous sodium hydroxide, with diethylamine in the presence of a coupling agent such as 1,3-dimethylaminopropyl-3-ethylcarbodiimide to yield the compound of formula (VII):

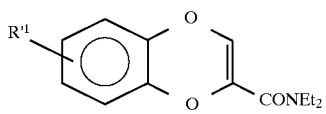

(VIII)

in which $R'^1$ has the same meaning as above, which is subjected to the action of a strong base and then trimethyltin chloride to yield the compound of formula (IX):

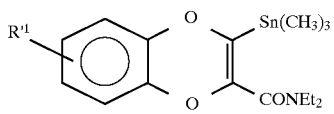

(IX)

in which $R'^1$ has the same meaning as above, which is condensed in the presence of copper iodide and a transition metal complex such as a palladium complex:

either with N-tert-butoxycarbonyl-2-iodoaniline to obtain the compound of formula (X):

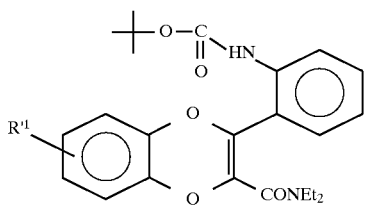

(X)

in which $R'^1$ has the same definition as above, which yields, after acid hydrolysis, the compound of formula (XI):

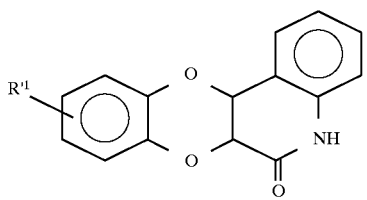

(XI)

in which $R'^1$ has the same definition as above, which is reacted with $POCl_3$ to obtain the compound of formula (I/a), a special case of the compounds of formula (I):

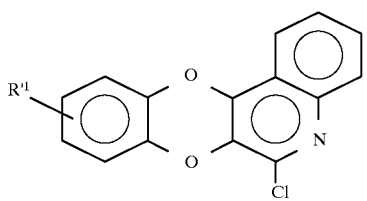

(I/a)

in which $R'^1$ is defined as above, which is subjected, in the case where $R'^1$ represents a linear or branched ($C_1$–$C_6$) alkoxy group, to a dealkylating agent such as boron tribromide, for example, to yield the compound of formula (I/b), a special case of the compounds of formula (I):

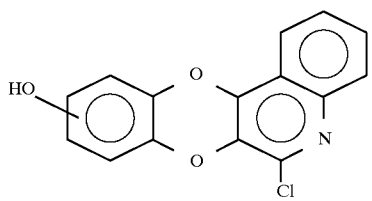

(I/b)

the collective compounds (I/a) and (I/b) forming the compound of formula (I/c), a special case of the compounds of formula (I):

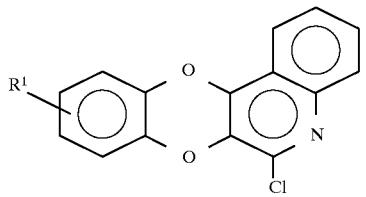

(I/c)

in which $R^1$ has the same meaning as in the formula (I), which compound of formula (I/c):

is subjected to a reducing agent such as zinc to yield the compound of formula (I/d), a special case of the compounds of formula (I):

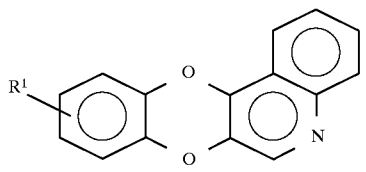

(I/d)

n which $R^1$ has the same meaning as above,
on which an N-alkylation is performed by the action of an alkylating agent such as methyl iodide to yield the compound of formula (I/e), a special case of the compounds of formula (I):

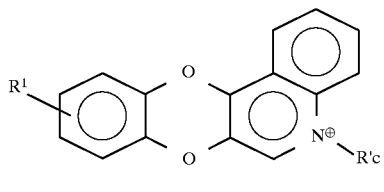

(I/e)

in which R'c represents a linear or branched $(C_1-C_6)$ alkyl group and Hal a halogen, or is condensed with diamines of formula HNR'aR'b where R'a represents a (linear or branched $(C_1-C_6)$ dialkyl) amino(linear or branched $(C_1-C_6)$) alkyl group, each alkyl portion being, independently of one another, identical or different, and R'b represents a hydrogen atom or a linear or branched $(C_1-C_6)$ alkyl group, to yield the compound of formula (I/f), a special case of the compounds of formula (I):

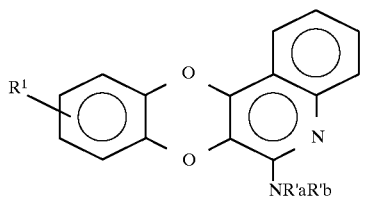

(I/f)

in which $R^1$, R'a and R'b have the same meanings as above, or with 2-iodotoluene to obtain the compound of formula (XII):

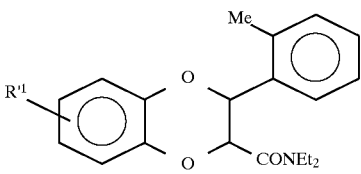

(XII)

in which $R'^1$ has the same meaning as above, which yields, after the action of a strong base such as lithium diisopropylamide, the compound of formula (I/g), a special case of the compounds of formula (I):

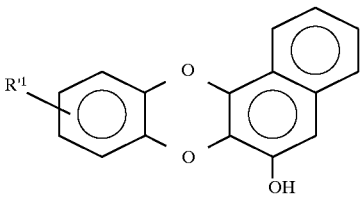

(I/g)

in which $R'^1$ is as defined above,
which compound of formula (I/g) is subjected:

in the case where $R'^1$ represents a linear or branched $(C_1-C_6)$ alkoxy group, to a dealkylating agent such as boron tribromide, for example, to yield the compound of formula (I/h), a special case of the compounds of formula (I):

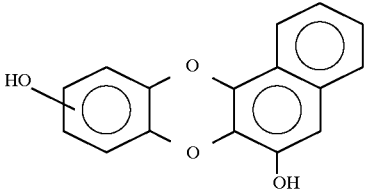

(I/h)

or to the successive action of trifluoromethanesulfonic anhydride, of a cyanide in the presence of a transition metal complex such as a palladium complex and of a reducing agent such as diisobutylaluminum hydride to obtain the compound of formula (I/i), a special case of the compounds of formula (I):

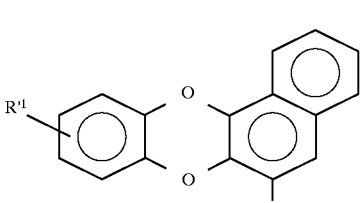

(I/i)

in which $R'^1$ has the same definition as above, which is oxidized to the methyl ester by the action of an oxidizing agent such as manganese dioxide in the presence of methanol to yield the compound of formula (I/j), a special case of the compounds of formula (I):

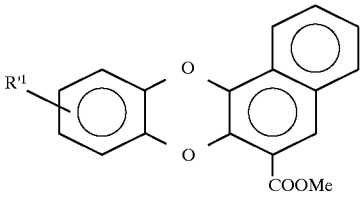

(I/j)

in which $R'^1$ has the same definition as above, which is reacted, in the case where $R'^1$ represents a linear or branched $(C_1-C_6)$ alkoxy group, with a dealkylating agent such as boron tribromide to yield the compound of formula (I/k), a special case of the compounds of formula (I):

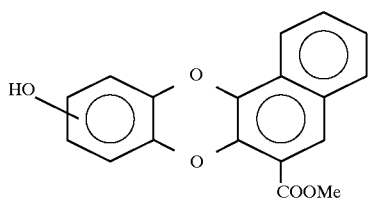
(I/k)

the collective compounds (I/j) and (I/k) forming the compound of formula (I/l), a special case of the compounds of formula (I):

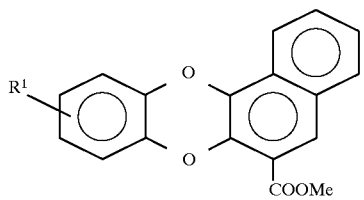
(I/l)

in which $R^1$ has the same definition as in the formula (I), which is condensed with diamines of formula HNR'aR'b where R'a represents a (linear or branched ($C_1$–$C_6$) dialkyl) amino(linear or branched ($C_1$–$C_6$)) alkyl group (each alkyl portion being identical or different), and R'b represents a hydrogen atom or a linear or branched ($C_1$–$C_6$) alkyl group, to yield the compound of formula (I/m), a special case of the compounds of formula (I):

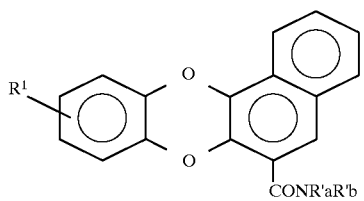
(I/m)

in which $R^1$, R'a and R'b have the same meaning as above, on the understanding that the compounds (I/m) may be obtained from the compound (I/k) subjected to electrophiles of formula $R'^1$-halogen where $R'^1$ is as defined above, in a basic medium, for the compounds in which X does not represent a nitrogen atom, the compound of formula (XIII):

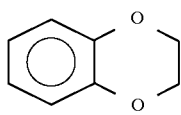
(XIII)

which is:

either dibrominated and then treated with meta-chloroperbenzoic acid and subjected to the action of potassium iodide to obtain the compound (XIIIa):

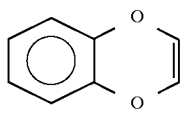
(XIIIa)

or acylated according to a Friedel-Crafts reaction, dibrominated, treated with meta-chloroperbenzoic acid and subjected to the action of sodium iodide and then of a base to obtain the compound (XIV):

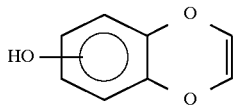
(XIV)

which is condensed with electrophiles of formula R'''-halogen in which R''' represents a linear or branched ($C_1$–$C_6$) alkyl group optionally substituted with an aryl or heteroaryl group, to yield the compound of formula (XV):

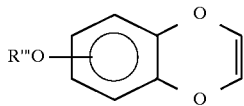
(XV)

in which R''' has the same definition as above, the collective compounds (XIIIa) and (XV) forming the compound of formula (XVI):

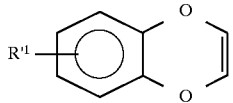
(XVI)

in which $R'^1$ represents a hydrogen atom or a linear or branched ($C_1$–$C_6$) alkoxy group optionally substituted with an aryl or heteroaryl group, which is condensed, after the action of a strong base such as butyllithium, for example, with electrophiles of formula (XVII):

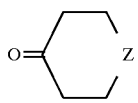
(XVII)

in which Z represents an NCOOEt group or a group

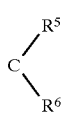

where $R^5$ and $R^6$ simultaneously represent a hydrogen atom or together form a ring

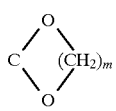

in which m equals 2 or 3, to yield the compound of formula (XVIII):

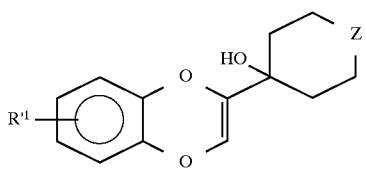
(XVIII)

in which $R'^1$ and Z have the same definition as above, which is dehydrated in the presence of mesyl chloride, for example, to obtain the compound of formula (XIX):

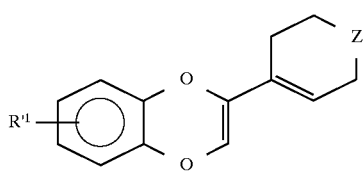

in which R'¹ and Z are as defined above, which is condensed with methyl acetylenedicarboxylate or methyl propiolate to obtain the compound of formula (XX):

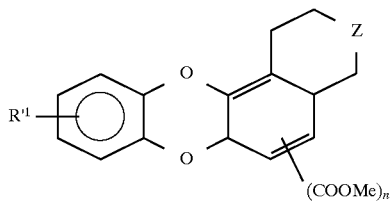

in which R'¹ and Z have the same meaning as above and n equals 1 or 2, which is subjected to the action of an oxidizing agent such as ortho-chloranil or 2,3-dichloro-5,6-dicyano-1,4-benzoquinone to yield the compound of formula (I/n), a special case of the compounds of formula (I):

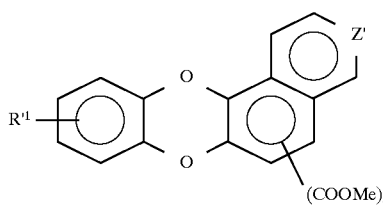

in which R'¹ and n have the same definition as above and Z' represents a nitrogen atom or a group C—R⁷ where R⁷ represents a hydrogen atom or a group O—(CH$_2$)$_m$—OH in which m equals 2or3, or the compound of formula (XXI):

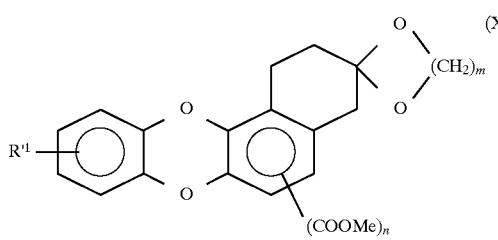

in which R'¹, n and m are as defined above, which is subjected successively to opening of the acetal in an acid medium, to the formation of a silyl ether, to oxidation with 2,3-dichloro-5,6-dicyano-1,4-benzoquinone and unblocking of the silyl ether with a fluorinated agent, to yield the compound of formula (I/o), a special case of the compounds of formula (I):

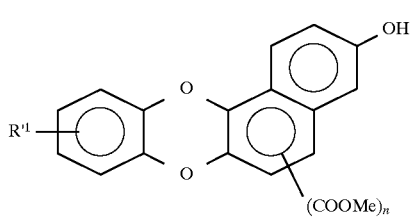

in which R'¹ and n have the same definition as above, which is condensed with various electrophiles R⁸-halogen where R⁸ represents a linear or branched (C$_1$–C$_6$) alkyl group optionally substituted with an aryl or heteroaryl group, to obtain the compounds of formula (I/p), a special case of the compounds of formula (I):

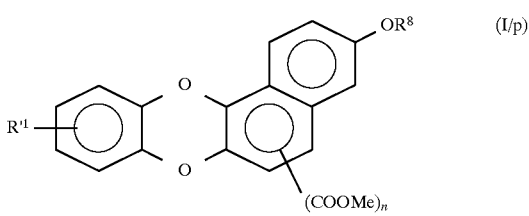

in which R'¹, n and R⁸ are as defined above, the compounds of formulae (I/n), (I/o) and (I/p) forming the collective compounds of formula (I/q), a special case of the compounds of formula (I):

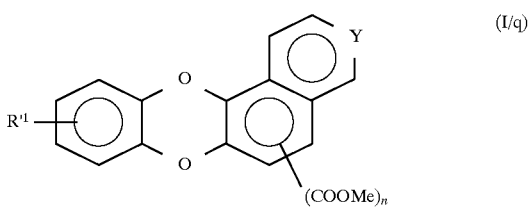

in which R'¹ and n are as defined above and Y has the same definition as in the formula (I), which compound (I/q):

when n equals 1 or 2, is condensed with diamines of formula HNR"aR"b in which R"a represents a (linear or branched (C$_1$–C$_6$) dialkyl)amino(linear or branched (C$_1$–C$_6$)) alkyl group (each alkyl portion being, independently of one another, identical or different) or a linear or branched (C$_1$–C$_6$) alkyl group substituted with at least one hydroxyl group, and R>>b represents a hydrogen atom or a linear or branched (C$_1$–C$_6$) alkyl group, to yield the compounds of formula (I/r), a special case of the compounds of formula (I):

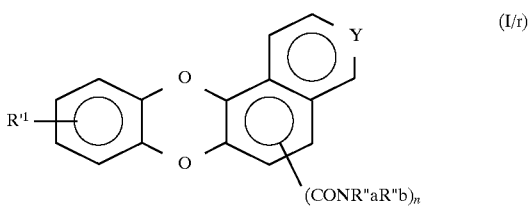

in which R'¹, R"a, R"b, n and Y have the same definition as above, or, when n equals 1 or 2, is subjected to reducing conditions to yield the corresponding alcohol, which undergoes an oxidation to aldehyde in the presence of manganese dioxide to yield the compound of formula (XXII):

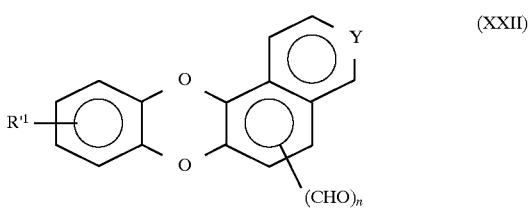

in which R'¹, Y and n are as defined above, which is condensed in the presence of zinc chloride and sodium cyanoborohydride with diamines of formula HNR"aR"b in which R"a represents a (linear or branched (C$_1$–C$_6$) dialkyl)amino(linear or branched (C$_1$–C$_6$)) alkyl group or a linear or branched (C$_1$–C$_6$) alkyl group substituted with at least one hydroxyl group, and R"b represents a hydrogen atom or a linear or branched ($C_1$–$C_6$) alkyl group, to yield the compounds of formula (I/s), a special case of the compounds of formula (I):

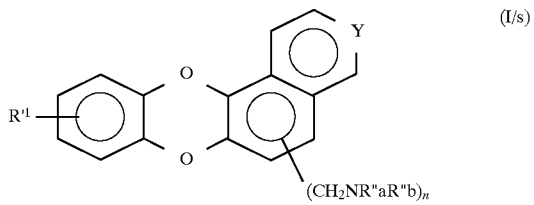

in which $R'^1$, R"a, R"b, Y and n have the same definition as above, or, when n equals 2, the compounds of formula (I/t), a special case of the compounds of formula (I):

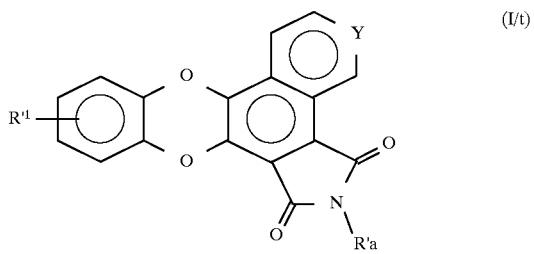

in which $R'^1$, R'a and Y have the same definition as above, the compounds (I/a-t) forming the collective compounds of the invention, which are purified, where appropriate, according to a standard purification technique, and which can, if so desired, be separated into their different optical or geometrical isomers or salified with a pharmaceutically acceptable acid or base.

The starting materials used in the process described above are commercial or readily accessible to a person skilled in the art according to processes well known in the literature, such as, for example, those described by J. Koo, S. Avakian, G. J. Martin, J. Am. Chem. Soc., 77, 1955, p. 5373.

The compounds of formula (I) possess advantageous pharmacological properties. They have excellent in vitro cytotoxicity, not only on leukemic lines but also on solid tumor lines; they also have an action on the cell cycle and are active in vivo on a leukemic model. These properties enable them to be used in therapy as antitumor agents.

The subject of the present invention is also pharmaceutical compositions containing the products of formula (I), their optical isomers or one of their addition salts with a pharmaceutically acceptable base or acid, alone or in combination with one or more nontoxic, inert excipients or vehicles.

Among the pharmaceutical compositions according to the invention, there will be mentioned, more especially, those which are suitable for oral, parenteral, nasal, rectal, perlingual, ocular or respiratory administration, and in particular simple or sugar-coated tablets, sublingual tablets, sachets or packets, hard gelatin capsules, preparations to be dissolved under the tongue, lozenges, suppositories, creams, ointments, skin gels, preparations to be injected or taken by mouth, aerosols and eye or nasal drops.

The appropriate dosage varies according to the patient's age and weight, the administration route, the nature of the therapeutic indication and of any associated treatments, and ranges between 0.1 and 400 mg daily in one or several administrations.

The examples which follow illustrate the invention and in no way limit it. The starting materials are products known or prepared according to known procedures.

EXAMPLE 1:

7,12-dioxa-5-azabenz[a]anthracene

Stare A: 1,4-Benzodioxin-2-carboxylic acid 1 mmol of ethyl 1,4-benzodioxin-2-carboxylate is brought to reflux in 25 ml of 8% sodium hydroxide solution. After cooling, 3N hydrochloric acid solution is added slowly until the benzodioxinic acid has precipitated. After filtration, the solid is recrystallized in benzene.

Melting point: 178°–180° C.

Stage B: 1,4-Benzodioxin-2-(diethylcarboxamide)

Under an inert atmosphere, 15.4 mmol of diethylamine, 15.4 mmol of 1,3-dimethylaminopropyl-3-ethylcarbodiimide and 15.4 mmol of hydroxybenzotriazole are added to a solution of 14.04 mmol of 1,4-benzodioxin-2-carboxylic acid in 25 ml of DMF at 0° C. The mixture is brought to room temperature and left stirring for 18 hours. After evaporation of the DMF, the residue is washed with water and then extracted with ethyl acetate. The organic phase is then dried over magnesium sulfate and concentrated under vacuum. The amide is purified by chromatography on silica gel (eluent: petroleum ether/ethyl acetate).

Stage C: 3-Trimethylstannyl-1,4-benzodioxin-2-(diethylcarboxamide)

At −78° C., under an inert atmosphere, 17.4 mmol of lithium diisopropylamide are added to 8.58 mmol of 1,4-benzodioxin-2-(diethylcarboxamide) in solution in 50 ml of anhydrous tetrahydrofuran. After 2 h 30 min of reaction, 21.4 mmol of trimethyltin chloride dissolved in a minimum of tetrahydrofuran are added dropwise. The reaction mixture is hydrolyzed after 3 hours and then extracted with ethyl acetate. The organic phase is dried over magnesium sulfate and concentrated under vacuum. The tin compound is purified by flash chromatography on silica gel treated with triethylamine.

Melting point: 63°–65° C.

Stage D: 3-[2-(t-Butyloxycarbonylamino)phenyl]-1,4-benzodioxin-2-(diethylcarboxamide)

Under an inert atmosphere, 3.93 mmol of 3-trimethylstannyl-1,4-benzodioxin-2-(diethylcarboxamide) and 3.94 mmol of N-t-butyloxycarbonyl-2-iodoaniline are dissolved in 25 ml of 1,4-dioxane. The reaction mixture is brought to reflux after adding 5% of palladium tetrakis (triphenylphosphine) and 5% of cuprous iodide. The solvent is evaporated off under vacuum and the residue is extracted with ethyl acetate. The organic phase is dried over magnesium sulfate and then concentrated under vacuum. The amide is purified by chromatography on silica gel (eluent: petroleum ether/ethyl acetate).

Melting point: 147°–149° C.

Stage E: [SH]-7,12-Dioxa-5-azabenz[a]anthracen-6-one 25 ml of 6N hydrochloric acid are added to 1.2 mmol of 3-[2-(t-butyloxycarbonylamion)phenyl]-1,4-benzodioxin-2-(diethylcarboxamide) in 25 ml of 1,4-dioxane. The mixture is heated to 70° C. for 8 hours. The volume of dioxane is reduced to one half under vacuum before the mixture is filtered. The solid is washed with water and then dried under vacuum in the presence of phosphorus pentoxide.

Melting point: >300° C.

Stage F: 6-Chloro-5-aza-7,12-dioxabenz[a]anthracene

Under an inert atmosphere, [5H]-7,12-dioxa-5-azabenz[a]anthracen-6-one is brought to reflux of phosphorus oxychloride for 6 hours. The solvent (phosphorus oxychloride) is then evaporated off under vacuum and the crude mixture is chromatographed by flash chromatography on silica gel (eluent: petroleum ether/ethyl acetate).

Melting point: 136°–138° C.

Stage G: 7,12-Dioxa-5-azabenz[a]anthracene

Under an inert atmosphere, 1 mmol of 6-chloro-5-aza-7,12-dioxabenz[a]anthracene and 8 mmol of powdered zinc are brought to 50° C. in 5 ml of acetic acid for 8 hours. After cooling, the reaction mixture is diluted in methanol and then filtered through Celite. The residue is concentrated under vacuum, then washed with saturated sodium hydrogen carbonate solution and then extracted with chloroform. The organic phase is dried over magnesium sulfate and concentrated under vacuum. The crude mixture is chromatographed by flash chromatography on silica gel (eluent: ethyl acetate/petroleum ether).

Melting point: 127°–129° C.

EXAMPLE 2:

$N^2$-(7,12-dioxa-5-azabenz[a]anthracen-6-yl)-$N^1$,$N^1$-dimethylethane-1,2-diamine Under an inert atmosphere, 6-chloro-5-aza-7,12-dioxabenz[a]anthracene (compound of Example 1—Stage F) is brought to reflux of N,N-dimethylethane-1,2-diamine for 2 hours. The excess diamine is evaporated off under vacuum and the residual crude product is chromatographed by flash chromatography on silica gel treated with triethylamine (eluent: ethyl acetate/methanol).

EXAMPLE 3:

$N^2$-(7,12-dioxa-5-azabenz[a]anthracen-6-yl)-$N^1$,$N^1$-diethylethane-1,2-diamine hydrochloride A solution of ether saturated with hydrochloric acid vapor is added to $N^2$-(7,12-dioxa-5-azabenz[a]anthracen-6-yl)-$N^1$,$N^1$-dimethylethane-1,2-diamine (compound of Example 2) dissolved in the minimum of dichloromethane. The corresponding hydrochloride obtained quantitatively is filtered off, washed with ether and then dried under vacuum.

Melting point: 280°–282° C.

EXAMPLE 4:

$N^2$-(7,12-dioxa-5-azabenz[a]anthracen-6-yl)-$N^1$,$N^1$-diethylethane-1,2-diamine hydrochloride The diamine is obtained according to the process of Example 2, with N,N-diethylethane-1,2-diamine and a reaction time of 3 hours, and the hydrochloride is obtained according to the process of Example 3.

Melting point: 256°–258° C.

EXAMPLE 5:

$N^2$-(7,12-dioxa-5-azabenz[a]anthracen-6-yl)-$N^1$,$N^1$-dimethylpropane-1,2-diamine hydrochloride The diamine is obtained according to the process of Example 2, with N,N-dimethylpropane-1,2-diamine, and the hydrochloride according to Example 3.

Melting point: 238°–240° C.

EXAMPLE 6:

$N^2$-(7,12-dioxa-5-azabenz[a]anthracen-6-yl)-$N^1$,$N^1$-diethylpropane-1,2-diamine hydrochloride The diamine is obtained according to the process of Example 2, with N,N-diethylpropane-1,2-diamine with a reaction time of 3 hours, and the hydrochloride according to the process of Example 3.

Melting point: 220°–222° C.

EXAMPLE 7:

10-methoxy-5-aza-7,12-dioxabenz[a]anthracene

Stage A: Ethyl 6-acetyl-1,4-benzodioxin-2-carboxylate 12.5 g of aluminum trichloride are added to a mixture of 4.27 g of acetyl chloride and 7.5 g of ethyl 1,4-benzodioxin-2-carboxylate in 150 ml of carbon disulfide at 0° C. The reaction mixture is stirred at room temperature for 14 hours. After acid hydrolysis with 50 ml of hydrochloric acid (2N) and extraction of the aqueous phase with dichloromethane, the organic phase is washed with saturated sodium hydrogen carbonate solution and then dried over magnesium sulfate. The acylated product is purified by chromatography on silica gel (eluent: petroleum ether/ethyl acetate, 7:3).

Melting point: 123°–125° C.

Stage B: Ethyl 6-acetyl-2,3-dibromo-1,4-benzodioxane-2-carboxylate

Under an inert atmosphere, at 0° C., 1.1 ml of elemental bromine in solution in 5 ml of carbon tetrachloride are added dropwise over 30 minutes to 5 g of ethyl 6-acetyl-1,4-benzodioxin-2-carboxylate partially solubilized in 50 ml of carbon tetrachloride. After 4 hours, the reaction medium is concentrated under vacuum. The dibromo compound is purified by flash chromatography on silica gel (eluent: petroleum ether/ ethyl acetate, 8:2).

Oil

Stage C: Ethyl 6-acetoxy-2,3-dibromo-1,4-benzodioxane-2-carboxylate

Under an inert atmosphere, 4 g of ethyl 6-acetyl-2,3-dibromo-1,4-benzodioxane-2-carboxylate are brought to reflux of dichloromethane in the presence of 5.6 g of meta-chloroperbenzoic acid for 72 hours. The chlorobenzoic acid formed is removed by filtration and the filtrate is washed with saturated potassium hydrogen carbonate solution and saturated sodium chloride solution. The organic phase is dried over magnesium sulfate and concentrated under vacuum. The crude mixture is chromatographed by flash chromatography on silica gel (eluent: petroleum ether/ ethyl acetate, 7:3).

Melting point: 58°–60° C.

Stage D: Ethyl 6-acetoxy-1,4-benzodioxin-2-carboxylate

Under an inert atmosphere, 6 g of ethyl 6-acetoxy-2,3-dibromo-1,4-benzodioxane-2-carboxylate in solution in 100 ml of acetone are mixed with 7.75 g of potassium iodide and stirred for 6 hours. After evaporation of the acetone under reduced pressure, the residue is diluted in ether and then washed with 20% sodium thiosulfate solution until the mixture is decolorized. The organic phase is then dried over magnesium sulfate and thereafter concentrated under vacuum. The compound is purified by chromatography on silica gel (eluent: petroleum ether/ethyl acetate, 7:3).

Melting point: 86°–88° C.

Stage E: Ethyl 6-hydroxy-1,4-benzodioxin-2-carboxylate

Under an inert atmosphere, 5 g of ethyl 6-acetoxy-1,4-benzodioxin-2-carboxylate in solution in 75 ml of ethanol and 3 ml of sodium ethanolate (IM) are stirred for 18 hours. The reaction medium is then neutralized with Dowex (X-8 acid form), thereafter filtered and concentrated under vacuum. The residual crude product is purified by chromatography on silica gel (eluent: petroleum ether/ethyl acetate, 7:3).

Melting point: 179°–181° C.

Stave F: Ethyl 6-methoxy-1,4-benzodioxin-2-carboxylate

Under an inert atmosphere, 2.4 g of ethyl 6-hydroxy-1,4-benzodioxin-2-carboxylate and 540 mg of sodium hydride in 25 ml of dimethylformamide are stirred at 0C. After 40 minutes, 0.84 ml of iodomethane are added dropwise and the mixture is then stirred for 1 hour at room temperature. The solvent is evaporated off under vacuum, and the residue is diluted in ethyl acetate and then washed with water. The organic phase is dried over magnesium sulfate and then concentrated under vacuum. The methyl ether is purified by chromatography on silica gel (eluent: petroleum ether/ethyl acetate, 7:3).

Melting point: 98°–100° C.

The compound of Example 7 is obtained by repeating Stages A, B, C, D, E, F and G of Example 1 starting from ethyl 6-methoxy- 1,4-benzodioxin-2-carboxylate.

Melting point: 132°–134° C.

EXAMPLE 8:

10-benzyloxy-5-aza-7,12-dioxabenz[a]anthracene

The same procedure is used as for Example 7, replacing methyl iodide in Stage F by benzyl chloride.

EXAMPLE 9:

$N^2$-(10-methoxy-7,12-dioxa-5-azabenz[a]anthracen-6-yl) -$N^1$,$N^1$-dimethylethane-1,2-diamine The compound of Example 9 is obtained by repeating Stages A, B, C, D, E and F of Example 7 and then Stages A, B, C, D, E and F of Example 1 starting from ethyl 6-methoxy-1,4-benzodioxin-2-carboxylate and Stage H (Example 2).

Melting point: 148°–150° C.

EXAMPLE 10:

$N^2$-(10-hydroxy-7,12-dioxa-5-azabenz[a]anthracen-6-yl)-$N^1$,$N^1$-dimethylethane-1,2-diamine hydrochloride Stare A: 10-Methoxy-6-chloro-5-aza-7,12-dioxabenz[a]anthracene The procedure is as for Stages A, B, C, D, E and F of Example 7 and then A, B, C, D, E and F of Example 1 taking as starting substrate ethyl 6-methoxy-1,4-benzodioxin-2-carboxylate.

Melting point: 194°–196° C.

Stage B: 10-Hydroxy-6-chloro-7,12-dioxa-5-azabenz[a]anthracene

Under an inert atmosphere and at 0C, 1.22 ml of boron tribromide are added dropwise to 80 mg of 10-methoxy-7, 12-dioxa-6-chloro-5-azabenz[a]anthracene in solution in 3 ml of dichloromethane. After 2 hours, the reaction mixture is hydrolyzed with saturated sodium carbonate solution. The organic phase is dried over magnesium sulfate and concentrated under vacuum. The demethylated compound is purified by chromatography on silica gel (eluent: petroleum ether/ethyl acetate, 7:3).

Melting point: >300° C.

Stare C: N2-(1O-Hydroxy-7,12-dioxa-5-azabenz[a]anthracen-6-yl)-$N^1$,$N^1$-dimethylethane-1,2-diamine hydrochloride The procedure is as for Example 2 for obtaining the diamine from 10-hydroxy-6-chloro-7,12-dioxa-5-azabenz[a]anthracene, and the corresponding hydrochloride is obtained using the procedure as described in Example 3.

Melting point: 273°–275° C.

EXAMPLE 11:

6-hydroxy-10-methoxy-7,12-dioxabenz[a]anthracene

Stage A: 3-Trimethylstannyl-6-methoxy-1,4-benzodioxin-2-(diethylcarboxamide)

The procedure is as for Stages A, B, C, D, E and F of Example 7 and then Stages A, B and C of Example 1 starting from ethyl 6-methoxy-1,4-benzodioxin-2-carboxylate.

Melting point: 58°–60° C.

Stage B.: 3-(2-Tolyl)-6-methoxy-1,4-benzodioxin-2-(diethylcarboxamide)

Under an inert atmosphere, 500 mg of 3-trimethylstannyl-6-methoxy-1,4-benzodioxin-2-(diethylcarboxamide) and 0.2 ml of iodotoluene are brought to reflux of 1,4-dioxane in the presence of 122 mg of palladium tetrakis and 22 mg of cuprous iodide for 3 hours. The dioxane is then evaporated off under vacuum and the residue is washed with water and then extracted with ethyl acetate. The organic phase is dried over magnesium sulfate and concentrated under vacuum. The coupling product is purified by flash chromatography on silica gel (eluent: toluene/ethyl acetate, 95:5).

Melting point: 60°–62° C.

Stage C: 6-Hydroxy-10-methoxy-7,12-dioxabenz[a]anthracene

Under an inert atmosphere, 1.42 ml of lithium diisopropylamide are added dropwise to 0.95 mmol of 3-(2-tolyl)-6-methoxy-1,4-benzodioxin-2-(diethylcarboxamide) in solution in 7 ml of THF at −78° C.. The reaction mixture is maintained at this temperature for 2 to 3 hours. The temperature is brought to -10° C. before acid hydrolysis (10% HCI). The aqueous phase is extracted with dichloromethane, and the organic phase is then dried over magnesium sulfate and concentrated under vacuum. The cyclized product is purified by flash chromatography on silica gel (eluent: toluene/ethyl acetate, 95:5).

Melting point: 183°–185° C.

| Elemental microanalysis: | C % | H % | O % |
|---|---|---|---|
| calculated | 72.85 | 4.32 | 22.83 |
| found | 72.57 | 4.61 | 22.86 |

EXAMPLE 12:

6,10-dihydroxy-7,12-dioxabenz[a]anthracene

Under an inert atmosphere, 0.1 ml of boron tribromide is added dropwise to 90 mg of 6-hydroxy-10-methoxy-7,12-dioxabenz[a]anthracene in solution in 3 ml of dichloromethane at 0° C. After 4 hours, the mixture is hydrolyzed. The organic phase is dried over magnesium sulfate and concentrated under vacuum. The bis-hydroxylated compound is purified by flash chromatography on silica gel (eluent: petroleum ether/ethyl acetate).

Melting point: 219°–221° C.

EXAMPLE 13:

10-hydroxy-7,12-dioxabenz[a]anthracene-6-[(2-dimethylaminoethyl)carboxamide] hydrochloride Stage A: Ethyl 6-isopropyloxy-1,4-benzodioxin-2-carboxylate The procedure used is the same as for Stages A, B, C, D, E and F of Example 7, with isopropyl iodide instead of methyl iodide.

Stage B: 3-Trimethylstannyl-6-isopropyloxy-1,4-benzodioxin-2-(diethylcarboxamide)

The procedure is as for Stages A, B and C of Example 1 starting from ethyl 6-isopropyloxy-1,4-benzodioxin-2-carboxylate.

Stage C: 6-Hydroxy-10-isopropyloxy-7,12-dioxabenz[a]anthracene

The procedure is as in Stages B and C of Example 11.

Stage D: 10-isopropyloxy-7,12-dioxabenz[a]anthracene 6-trifluoromethanesulfonic ester Under an inert atmosphere, 0.1 ml of pyridine and then 0.45 ml of triflic anhydride are added dropwise at 0° C. to $^6$-hydroxy-10-isopropyloxy-7,12-dioxabenz-[a]anthracene in solution in 10 ml of dichloromethane. After 1 hour, the reaction mixture is hydrolyzed with saturated ammonium chloride solution. An extraction is performed with dichloromethane, and the organic phase is then dried over magnesium sulfate and concentrated under vacuum. Purification is carried out by flash chromatography on silica gel (eluent: petroleum ether/ ethyl acetate, 9:1).

Melting point: 98°–100° C.

Stage E: 6-Cyano-10-isopropyloxy-7,12-dioxabenz[a]anthracene

Under an inert atmosphere, 27 mg of zinc cyanide and 420 mg of palladium tetrakis are added successively to the triflic compound in solution in 3 ml of DMF. The reaction mixture is then heated to 80° C. for 30 minutes. After evaporation of the DMF under reduced pressure, the residue is washed with saturated sodium carbonate solution and then extracted with ethyl acetate. The organic phase is dried over magnesium sulfate and concentrated under vacuum. A purification is performed by flash chromatography on silica gel (eluent: petroleum ether/ethyl acetate, 95:5).

Melting point: 133°–135° C.

Stage F: 10-Isopropyloxy-7, 12-dioxabenz[a]anthracene-6-carbaldehyde

Under an inert atmosphere, 0.8 ml of diisobutylaluminum hydride is added dropwise to 170 mg of 6-cyano-10-isopropyloxy-7,12-dioxabenz[a]anthracene in solution in 5 ml of toluene at room temperature. After 15 minutes, the reaction mixture is hydrolyzed with 5% hydrochloric acid solution. The aqueous phase is extracted with dichloromethane, and the organic phase is then dried over magnesium sulfate and concentrated under vacuum. The aldehyde is purified by flash chromatography on silica gel (eluent: petroleum ether/ethyl acetate, 95:5).

Melting point: 140°–142° C.

Stage G: 10-Isopropyloxy-7,12-dioxabenz[a]anthracene 6-carboxymethyl ester

Under an inert atmosphere, 84 mg of sodium cyanide, 597 mg of manganese dioxide and 82 mg of glacial acetic acid are added to 1410 mg of 10-isopropyloxy-7,12-dioxabenz[a]anthracene-6-carbaldehyde in solution in 5 ml of anhydrous methanol. The reaction mixture is brought to 40° C. for 6 hours before being filtered. The filtrate is washed with water and then extracted with dichloromethane. The organic phase is dried over magnesium sulfate and concentrated under vacuum. The methyl ester is purified by chromatography on silica gel (eluent: petroleum ether/ethyl acetate, 9:1).

Melting point: 128°–130° C.

Stage H: 10-Hydroxy-7,12-dioxabenz[a]anthracene 6-carboxymethyl ester

Under an inert atmosphere, 0.04 ml of boron tribromide is added to 50 mg of the isopropyl ether (Stage G) in solution in 2 ml of dichloromethane at −10° C. After 15 minutes, the reaction mixture is hydrolyzed. The aqueous phase is extracted with dichloromethane, then dried over magnesium sulfate and concentrated under vacuum. The hydroxyl compound is purified by chromatography on silica gel (eluent: petroleum ether/ethyl acetate, 7:3).

Melting point: 168°–170° C.

Stage I: 10-Hydroxy-7,12-dioxabenz[a]anthracene-6-[(2-dimethylaminoethyl) carboxamide] hydrochloride The procedure is as for Examples 2 and 3.

Melting point: decomposition from 130° C.

EXAMPLE 14:

10-methoxy-7,12-dioxabenz[a]anthracene-6-[(2-dimethylaminoethyl)carboxamide] hydrochloride Stage A: 10-Methoxy-6-hydroxy-7,12-dioxabenz[a]anthracene The procedure is as for Example 11.

Melting point: 183°–185° C.

Stage B: 10-Methoxy-7,12-dioxabenz[a]anthracene 6-carboxymethyl ester

The procedure is according to Stages D, E, F and G of Example 13.

Melting point: 108°–110° C.

Stage C: 10-Methoxy-7,12-dioxabenz[a]anthracene-6-[(2-dimethylaminoethyl) carboxamide] hydrochloride The procedure is as in Examples 2 and 3.

Melting point: 213°–215° C.

EXAMPLE 15:

7,12-dioxabenz[a]anthracene-5-[(2-dimethylaminoethyl)carboxamide]

Stage A: 1,4-Benzodioxin

Under an inert atmosphere, 57.9 g of N-bromosuccinimide and 30 mg of azaisobutyronitrile are added to a solution of 20 g of 1,4-benzodioxane in 300 ml of carbon tetrachloride. The reaction mixture is brought to reflux using a lamp for 6 hours. The succinimide formed is removed by filtration and the filtrate is concentrated under vacuum. The product obtained is dissolved in 250 ml of acetone and stirred for 2 hours in the presence of 108 g of sodium iodide. After evaporation of the solvent, the green residue is dissolved in a water/ether mixture, and the organic phase is then washed with 20% sodium thiosulfate solution and dried over magnesium sulfate. The benzodioxin is purified by chromatography on silica gel.

Stage B: 2-(1-Hydroxy-l-cyclohexyl)-1,4-benzodioxin

Under an inert atmosphere, 16.79 ml of a 1.6M solution of n-butyllithium in hexane are added to a solution of 3 g of 1,4-benzodioxin in 50 ml of anhydrous THF at −78° C.

After 1 hour, 30 mmol of cyclohexanone are added dropwise. The temperature is maintained at −78° C. for 3 hours 30 minutes. After hydrolysis and neutralization of the reaction medium with 10% hydrochloric acid solution, the aqueous phase is extracted with ether and the organic phase is then dried over magnesium sulfate and concentrated under vacuum. The alcohol is purified by chromatography on silica gel (eluent: petroleum ether/ethyl acetate) in the form of an oil.

Stage C: 2-(1-Cyclohexenyl)-1,4-benzodioxin

Under an inert atmosphere, 14 ml of triethylamine and 3.85 ml of mesyl chloride are added slowly to a solution of 10 ml of 2-(1-hydroxy-1-cyclohexyl)-1,4-benzodioxin in 75 ml of dichloromethane at 0° C. The mixture is brought to reflux after 15 minutes for 1.5 hours. After hydrolysis, an extraction with dichloromethane is carried out, and the organic phase is then dried over magnesium sulfate and concentrated under vacuum. The diene is purified by chromatography on silica gel (eluent: petroleum ether/ethyl acetate, 7:3) in the form of an oil.

Stage D: Methyl 1,2,3,4,4a,6a-hexahydro-7,12-dioxabenz[a]anthracene-5-carboxylate In a sealed tube, 500 mg of 2-(1-cyclohexenyl)-1,4-benzodioxin and 1.4 ml of methyl propiolate are stirred for 22 hours 30 minutes at 70° C. The regioisomers are separated by chromatography on silica gel (eluent: petroleum ether/ethyl acetate, 98:2).
Melting point: 72°–74° C.

Stage E: Methyl 7, 12-dioxabenz[a]anthracene-5-carboxylate

Under an inert atmosphere, 370 mg of methyl 1,2,3,4,4a,6a-hexahydro-7,12-dioxabenz[a]anthracene-5-carboxylate in solution in 10 ml of toluene are brought to reflux for 6 hours in the presence of 986 mg of DDQ. After cooling, the reaction mixture is washed with 8% sodium hydroxide solution. The organic phase is dried over magnesium sulfate and then concentrated under vacuum. Purification is performed by chromatography on silica gel (eluent: petroleum ether/ethyl acetate, 95:5).
Melting point: 144°–146° C.

Stake F: 7,1$^2$-Dioxabenz[a]anthracene-5-[(2-dimethylaminoethyl)carboxamide]

The procedure is as for Example 2.
Melting point: 198°–200° C.

EXAMPLE 16:

7,12-dioxabenz[a]anthracene-6-[(2-dimethylaminoethyl)carboxamide]

The procedure is as in Example 15, choosing the other regioisomer at Stage D.
Melting point: 139°–141° C.

EXAMPLE 17:

$N^2$-(7,12-dioxabenz[a]anthracene-5,6-maleimido)-$N^1$,$N^1$-dimethylethylenediamine hydrochloride Stage A: Methyl 7, 12-dioxabenz[a]anthracene-5,6-dicarboxylate The procedure is according to Stages A, B, C, D and E of Example 15, using methyl acetylenedicarboxylate in place of methyl propiolate in Stage D.
Melting point: 182°–184° C.

Stage B: $N^2$-(7,12-Dioxabenz[a]anthracene-5,6-maleimido)-$N^1$,$N^1$-dimethylethylenediamine Under an inert atmosphere, 600 mg of methyl 7,12-dioxabenz[a]anthracene-5,6-dicarboxylate are brought to 100° C. in 10 ml of N,N-dimethylethylenediamine for 24 hours. The compound obtained is purified by chromatography on silica gel (eluent: ethyl acetate/methanol, 85:15).
Melting point: 186°–188° C.

Stage C: $N^2$-(7,12-Dioxabenz[a]anthracene-5,6-maleimido)-$N^1$,$N^1$-dimethylethylenediamine hydrochloride The procedure is a s in Example 3.
Melting point: 208°–210° C.

EXAMPLE 18:

$N^2$-(7,12-dioxa-3-azabenz[a]anthracene-5,6-maleimido)-$N^1$,$N^1$-dimethylethylenediamine hydrochloride Stare A: 1,2,4,4a,6a-Pentahydro-7,12-dioxa-3-azabenz[a]anthracene 3-(ethyl carboxylate) 5,6-(methyl dicarboxylate)

The procedure is according to Stages A, B, C and D of Example 15, replacing cyclohexanone by N-carbethoxy4-piperidone in Stage B and methyl propiolate by methyl acetylenedicarboxylate in Stage D.

Stage B.: 1,2,4-Trihydro-7,12-dioxa-3-azabenz[a]anthracene 3-(ethyl carboxylate) 5,6-(methyl dicarboxylate)

Under an inert atmosphere, 1.5 g of 1,2,4,4a,6a-pentahydro-7,12-dioxa-3-azabenz[a]anthracene 3-(ethyl carboxylate) 5,6-(methyl dicarboxylate) are dissolved in 25 ml of toluene. The solution is brought to 35° C. after adding 1.196 g of ortho-chloranil for 48 hours. After cooling, the reaction mixture is washed with 8% sodium hydroxide solution. The organic phase is dried over magnesium sulfate and then concentrated under vacuum. Purification is performed by chromatography on silica gel (eluent: petroleum ether/ethyl acetate, 6:4).
Melting point: 153°–155° C.

Stage C: Methyl 7, 12-dioxa-3-azabenz[a]anthracene-5,6-dicarboxylate

Under an inert atmosphere, 1 g of 1,2,4trihydro-7,12-dioxa-3-azabenz[a]anthracene 3-(ethyl carboxylate) 5,6-(methyl dicarboxylate) is brought to reflux in 25 ml of toluene in the presence of 1.574 g of ortho-chloranil for 48 hours. The procedure is thereafter as for Stage B.
Melting point: 160°–162° C.

Stage D: $N^2$-(7,12-Dioxa-3-azabenz[a]anthracene-5,6-maleimido)-$N^1$,$N^1$-dimethylethylenediamine hydrochloride The procedure is as for Stages B and C of Example 17.
Melting point: 278°–280° C.

EXAMPLE 19:

$N^2$-[7,12-dioxa-3-(2-hydroxyethoxy)benz[a]anthracene-5,6-maleimido]-$N^1$,$N^1$-dimethylethylenediamine hydrochloride Stage A: Methyl 7, 12-dioxa-3-(2-hydroxyethoxy)benz[a]anthracene-5, 6-dicarboxylate The procedure is as for Stages A, B, C, D and E of Example 15, replacing cyclohexanone by 1,4-cyclohexanedione monoethylene acetal in Stage B and methyl propiolate by methyl acetylene dicarboxylate in Stage D.
Melting point: 182°–184° C.

Stage B: $N^2$-[7, 12-Dioxa-3-(2-hydroxyethoxy)benz[a]anthracene-5, 6-maleimido]-$N^1$,$N^1$-dimethylethylenediamine hydrochloride The procedure is as for Stages B and C of Example 17.
Melting point: 298°–300° C.

EXAMPLE 20:

$N^2$-(7,12-dioxa-3-hydroxybenz[a]anthracene-5,6-maleimido)-$N^1$,$N^1$-dimethylethylenediamine hydrochloride Stage A: Methyl 1,2,4-trihydro-7,12-dioxa-3-(ethylene acetal)benz[a]anthracene-5,6-dicarboxylate The procedure is as for Stage A of Example 19.
Melting point: 144°–146° C.

Stage B: Methyl 1,2,4-trihydro-7, 12-dioxa-3-oxobenz[a]anthracene-5, 6-dicarboxylate Under an inert atmosphere, 1 g of acetal is brought to reflux of acetone in the presence of 609 mg of para-toluenesulfonic ester. After 72 hours, the solvent is evaporated off under vacuum, the reaction mixture is washed with water and then extracted with ethyl acetate. The organic phase is dried over magnesium sulfate and concentrated under vacuum. The ketone is purified by chromatography on silica gel (eluent: petroleum ether/ethyl acetate, 6:4).
Melting point: 190°–192° C.

Stage C: Methyl 1,2-dihydro-7,12-dioxa-3-(tert-butyldimethylsilyl ether)benz[a]anthracene-5,6-dicarboxylate Under an inert atmosphere, 1 ml of lithium diisopropylamide and 0.3 ml of tetramethylethylenediamine are added dropwise successively to 500 mg of ketone (Stage B) solubilized in 10 ml of tetrahydrofuran and 0.5 ml of hexamethylphosphoramide at −78° C. The mixture is maintained at -78° C. for 2 hours before adding 415 mg of dimethyl-tert-butylsilane chloride dissolved in a minimum of tetrahydrofuran. After 3 hours, the reaction mixture is brought to -10° C. and the volatile products are then evaporated off under reduced pressure. The silyl ether is purified by flash chromatography on silica gel treated with triethylamine (eluent: petroleum ether/ethyl acetate, 9:1).
Melting point: 98°–100° C.

Stage D: Methyl 7,12-dioxa-3-(tert-butyldimethylsilyl ether)benz[a]anthracene-5,6-dicarboxylate The procedure is as for Stage E of Example 15.
Melting point: 68°–70° C.

Stage E: Methyl 3-hydroxy-7,12-dioxabenz[a]anthracene-5,6-dicarboxylate

Under an inert atmosphere, 450 mg of silyl ether (Stage D) are dissolved in tetrahydrofuran before adding 1.9 ml of tetra-tert-butylammonium fluoride at room temperature. After 30 minutes, the reaction mixture is washed with water. The aqueous phase is extracted with dichloromethane, and the organic phase is dried over magnesium sulfate and concentrated under vacuum. The hydroxyl compound is purified by chromatography on silica gel (eluent: petroleum ether/ethyl acetate, 5:5).
Melting point: 198°–200° C.

Stage F: $N^2$-(7,12-Dioxa-3-hydroxybenz[a]anthracene-5,6-maleimido)-$N^1$,$N^1$-dimethylethylenediamine hydrochloride The procedure is as for Stages B and C of Example 17.
Melting point: 298°–300° C.

EXAMPLE 21:

$N^2$-(7,12-dioxa-3-methoxybenz[a]anthracene-5,6-maleimido)-$N^1$,$N^1$-dimethylethylenediamine hydrochloride Stave A: Methyl 3-hydroxy- 7, 12-dioxabenz[a]anthracene-5, 6-dicarboxylate The procedure is as for Stages A, B, C, D and E of Example 20.

Stage B: Methyl 3-methoxy- 7, 12-dioxabenz[a]anthracene-5, 6-dicarboxylate

The procedure is as in Stage F of Example 7.
Melting point: 170°–172° C.

Stage C: A2-(7, 12-Dioxa-3-methoxybenz[a]anthracene-5, 6-maleimido)-$N^1$,$N^1$-dimethylethylenediamine hydrochloride The procedure is as for Stages B and C of Example 17.
Melting point: 258°–260° C.

EXAMPLE 22:

$N^2$-(7,12-dioxa-3-benzyloxybenz[a]anthracene-5,6-maleimido)-$N^1$,$N^1$-dimethylethylenediamine hydrochloride The procedure is as for Example 21, replacing Stage F of Example 7 by the procedure of Example 8.

EXAMPLE 23:

7,12-dioxa-3-hydroxybenz[a]anthracene-5,6-[(2-dimethylaminoethyl) carboxamide] hydrochloride The procedure is as for Example 20.
Melting point: decomposition at 160° C.

EXAMPLE 24:

7,12 oxabenz[a]anthracene-6-[(1,3-hydroxy-3-methylpropyl) carboxamide

Stage A: Methyl 7, 12-dioxabenz[a]anthracene-6-carboxylate

The procedure is as in Example 15 up to Stage E, choosing the other regioisomer at Stage D.

Stage B: 7, $1^2$-Dioxabenz[a]anthracene-6-[(1,3-dihydroxy-3-methylpropyl)carboxamide]

Under an inert atmosphere, 70 mg of methyl 7,12-dioxabenz[a]anthracene-6-carboxylate dissolved in 3 ml of tetrahydrofuran are brought to reflux in the presence of 251 mg of 2-methyl-2-amino-1,3-propanediol for 76 hours. The compound is purified by chromatography on silica gel neutralized with triethylamine (eluent: ethyl acetate/methanol, 9:1).
Melting point: 136°–138° C.

EXAMPLE 25:

7,12-dioxabenz[a]anthracene-5-[(2dimethylaminoethyl)methylamine] hydrochloride

Stare A: Methyl 7,12-dioxabenz[a]anthracene-5-carboxylate

The procedure is as for Stages A, B, C, D, E and F of Example 15.

Stage B: 7,12-Dioxabenz[a]anthracen-5-ylmethanol

Under an inert atmosphere, 72 mg of lithium aluminum hydride and 170 mg of the compound of Stage A dissolved in 5 ml of tetrahydrofuran are stirred at room temperature for 45 minutes. The reaction mixture is then hydrolyzed and the aqueous phase is extracted with ethyl acetate. The organic phase is dried over magnesium sulfate and concentrated under vacuum. The compound is purified by flash chromatography on silica gel (eluent: petroleum ether/ethyl acetate, 7:3).
Melting point: 189°–191° C.

Stage C: 7,12-Dioxabenz[a]anthracen-5-carbaldehyde 130 mg of alcohol and 642 mg of manganese dioxide dissolved in 10 ml of dichloromethane are stirred for 3 hours at room temperature, and the solution is then filtered. The filtrate is concentrated under vacuum and purified by chromatography on silica gel (eluent: petroleum ether/ethyl acetate, 9:1).
Melting point: 133°–135° C.

Stage D: 7,12-Dioxabenz[a]anthracene-5-[(2-dimethylaminoethyl)methylamine]

Under an inert atmosphere, 34 mg of zinc chloride and 32 mg of sodium cyanoborohydride dissolved in 1 ml of methanol are added to a solution in 5 ml of methanol of 130 mg of aldehyde and 0.22 ml of dimethylethylenediamine. After 6 hours at 35° C., the methanol is evaporated off. The residue is taken up in dichloromethane and washed with water. The organic phase is dried over magnesium sulfate and concentrated under vacuum. The compound is purified by chromatography on silica gel treated with triethylamine (eluent: ethyl acetate/methanol, 9:1)

Stage E: 7,12-Dioxabenz[a]anthracene-5-[(2-dimethylaminoethyl)methylamine] hydrochloride The procedure is as in Example 3.
Melting point: 254°–256° C.

EXAMPLE 26:

7,12-dioxabenz[a]anthracene-6-[(1,3-dihydroxy-3-methylpropyl)methylamine

The procedure is as for Stages A, B, C, D and E of Example 15 to obtain methyl 7,12-dioxabenz[a]anthracene- 6-carboxylate, which is treated according to the processes of Stages B, C and D of Example 25, using 2-methyl-2-amino-1,3-propanediol as amine in Step D.
Melting point: 148°–150° C.

EXAMPLE 27:

7,12-dioxa-5-aza-5-methylbenz[a]anthracene iodide

The procedure is as in Example 1 of Stages A, B, C, D, E, F and G, and the 140 mg of 7,12-dioxa-5-azabenz[a]anthracene is treated with 1.85 ml of methyl iodide. After 12 hours at room temperature protected from light, the precipitated product is isolated by filtration.
Melting point: 263°–265° C.

EXAMPLE 28:

$N^2$-(8-methoxy-7,12-dioxa-5-azabenz[a]anthracen-6-yl)-$N^1$,$N^1$-dimethylethane-1,2-diamine hydrochloride The procedure is as for Stages A, B, C, D, E and F of Example 7 and then A, B, C, D, E and F of Example 1, taking as starting substrate ethyl 8-methoxy-1,4-benzodioxin-2-carboxylate to yield the corresponding compound chlorinated at position 6, which is treated according to the procedure of Example 2 to obtain the diamine, and the corresponding hydrochloride is obtained using the procedure described in Example 3.
Melting point: 256°–258° C.

EXAMPLE 29:

$N^2$-(8-hydroxy-7,12-dioxa-5-azabenz[a]anthracen-6-yl)-$N^1$,$N^1$-dimethylethane-1,2-diamine hydrochloride The procedure is as for Stages A, B and C of Example 10, taking ethyl 8-methoxy-1,4-benzodioxin-2-carboxylate as starting substrate for Stage A.
Melting point: 286°–288° C.

EXAMPLE 30:

$N^2$-(11-methoxy-7,12dioxa-5-azabenz[a]anthracen-6-yl)-$N^1$,$N^1$-dimethylethane-1,2-diamine hydrochloride The procedure is as in Example 28, taking ethyl 5-methoxy- 1,4-benzodioxin-2-carboxylate as starting substrate.
Melting point: 271°–273° C.

EXAMPLE 31:

$N^2$-(11-hydroxy-7,12-dioxa-5-azabenz[a]anthracen-6-yl)-$N^1$,$N^1$-methylethane-1,2-diamine hydrochloride The procedure is as in Example 29, taking ethyl 5-methoxy-1,4-benzodioxin-2-carboxylate as starting substrate.
Melting point: 265°–267° C.

PHARMACOLOGICAL STUDY

The examples which follow enable the cytotoxic properties of the compounds of the invention, their action on the cell cycle and in vivo on a leukemic model to be demonstrated.

EXAMPLE A

Cytotoxicity of the compounds

Three cell lines were used:
1 murine leukemia, L1210,
1 human epidermoid carcinoma, KB-3°–1,
1 non-small-cell human pulmonary carcinoma, A549.

The cells are cultured in complete RPMI 1640 culture medium containing 10% of fetal calf serum, 2 mM glutamine, 50 units/ml of penicillin, 50 μg/ml of streptomycin and 10 mM HEPES.

The cells are distributed in microplates and exposed to the cytotoxic compounds. They are then incubated for 2 days (L1210) and 4 days (A549, KB-3-1). The number of viable cells is then quantified by a colorimetric assay, the Minoculture Tetrazolium Assay (Carmichael J., De Graff W. G., Gazdar A. F., Minna J. D. and Mitchell J. R., Evaluation of a tetrazolium-based semi-automated colorimetric assay: assessment of chemosensitivity testing, Cancer Res., 47, 936–942, 1987). The results are expressed as an $IC_{50}$, the concentration of cytotoxic compound which inhibits the proliferation of the treated cells by 50%.

The results obtained show a good general cytotoxicity on the L1210 line, with $IC_{50}$ values of between 0.2 and 1 μM. Moreover, it was possible to demonstrate cytotoxic properties with respect to solid tumors such as the KB-3-1 line and the A549 line.

EXAMPLE B

Action on the cell cycle

L1210 cells are incubated for 21 hours at 37° C. in the presence of different concentrations of test products. The cells are then fixed with 70% (V/V) ethanol, washed twice in PBS and incubated for 30 minutes at 20° C. in PBS containing 100 μg/ml of RNAse and 50 μg/ml of propidium iodide. The percentage in G2+M phase is calculated, and the results are expressed according to a classification determined as a function of the percentage of cells accumulated in G2+M phase after 21 hours relative to the control (control: 20%). The compounds of the invention show a more than 70% accumulation of the cells in G2+M phase after 21 hours for concentrations of products ranging from 0.5 to 50 μM.

EXAMPLE C

In vivo activity: antitumor activity on P388 leukemia

The P388 (murine leukemia) line was supplied by the National Cancer Institute (Frederick, USA). The tumor cells ($10^6$ cells) were inoculated on day 0 into the peritoneal cavity of female BDF1 mice (Iffa-Credo, France) weighing from 18 to 20 g (groups of 8 to 10 animals). The products were administered on day 1 at the indicated doses via the intraperitoneal route. The antitumor activity is expressed as a percentage of T/C:

$$\% \, T/C = \frac{\text{Median survival time of the treated animals}}{\text{Median survival time of the control animals}} \times 100$$

The results obtained show excellent in vivo activity on the P388 leukemic model, with, for example, a T/C of 196% for a dose of 50 mg/kg, as well as a low cytotoxicity of the compounds, testifying to an excellent therapeutic index.

EXAMPLE D

Tablets containing a 10 mg dose of $N^2$-(7,12-dioxa-3-hydroxybenz[a] anthracene-5,6-maleimido)-$N^1$, $N^1$-dimethylethylenediamine hydrochloride (Example 20)

Preparation formula for 1000 tablets:

N²-(7,12-dioxa-3-hydroxybenz[a]anthracene-5,6-
maleimido)-n¹,n¹-dimethylethylene—
diamine .................................................. 10 g
Wheat starch ............................................ 15 g
Corn starch .............................................. 15 g
Lactose .................................................... 65 g
Mg stearate ............................................... 2 g
Silica ........................................................ 1 g
Hydroxypropylcellulose ............................ 2 g

We claim:

1. A compound selected from those of the formula (I):

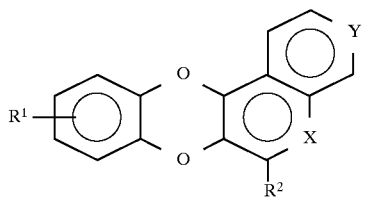

in which:
R¹ represents hydrogen or a group of formula O—R, in which R represents hydrogen or linear or branched ($C_1$–$C_6$) alkyl (optionally substituted with aryl or heteroaryl),
R² represents hydrogen, halogen, hydroxyl, linear or branched ($C_1$–$C_6$) alkoxy, formyl, $CF_3SO_3$, cyano, linear or branched ($C_1$–$C_6$) alkoxycarbonyl, aryloxycarbonyl, NR'aR'b in which R'a represents ($C_1$–$C_6$) dialkylaminoalkyl (each alkyl portion consisting, independently of one another, of an identical or different, linear or branched chain containing 1 to 6 carbon atoms inclusive) and R'b represents hydrogen or linear or branched ($C_1$–$C_6$) alkyl, or BNR"aR"b in which B represents carbonyl or methylene, R"a and R"b have the same definition as R'a and R'b, respectively, or R"a represents linear or branched ($C_1$–$C_6$) alkyl substituted with at least one hydroxyl,
X represents nitrogen (optionally substituted with a linear or branched ($C_1$–$C_6$) alkyl group designated R'c), or C—R³ in which R³ represents hydrogen, linear or branched ($C_1$–$C_6$) alkoxycarbonyl or BNR"aR"b in which B represents carbonyl or a methylene and R"a and R"b have the same definition as above,
or R² and X, when X represents C—R³, with the carbon atom which bears them, together form a ring of formula (II):

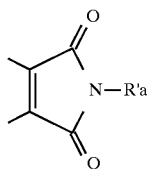

in which R'a has the same definition as above,
Y represents nitrogen or C—R⁴ in which R⁴ represents hydrogen, or a group of formula O–R" in which R" represents hydrogen, linear or branched ($C_1$–$C_6$) alkyl (optionally substituted with hydroxyl) or aryl or heteroaryl, on the understanding that, when X represents nitrogen and Y a CH group, or when X represents CH and Y nitrogen, or when X and Y simultaneously represent CH, then R' and R² cannot simultaneously represent hydrogen,
on the understanding that the term aryl means a phenyl or naphthyl group optionally substituted in an identical or different manner with one or more halogen or linear or branched ($C_1$–$C_6$) alkyl, hydroxyl, linear or branched ($C_1$–$C_6$) alkoxy or trihalomethyl, and the term heteroaryl means a mono- or bicyclic aromatic group containing 1 or 2 hetero atoms chosen from O, S and N, optionally substituted in an identical or different manner with one or more halogen or linear or branched ($C_1$–$C_6$) alkyl, hydroxyl, linear or branched ($C_1$–$C_6$) alkoxy, or trihalomethyl,
its isomers as well as its addition salts with a pharmaceutically acceptable acid or base.

2. A compound of claim 1, in which R² represents NR'aR'b in which R'a represents (linear or branched ($C_1$–$C_6$) dialkyl)amino(linear or branched ($C_1$–$C_6$)) alkyl, each alkyl portion being, independently of one another, identical or different, and R'b represents hydrogen or linear or branched ($C_1$–$C_6$) alkyl, its isomers as well as its addition salts with a pharmaceutically acceptable acid or base.

3. A compound of claim 1, in which R² represents BNR"aR"b in which B represents carbonyl or methylene, R"a represents (linear or branched ($C_1$–$C_6$) dialkyl)amino-(linear or branched ($C_1$–$C_6$)) alkyl, each alkyl portion being, independently of one another, identical or different, and R"b represents hydrogen or linear or branched ($C_1$–$C_6$) alkyl, its isomers as well as its addition salts with a pharmaceutically-acceptable acid or base.

4. A compound of claim 1, in which X represents C—R³ in which R³ represents BNR"aR"b in which B represents carbonyl or methylene, R"a represents (linear or branched ($C_1$–$C_6$) dialkyl)amino(linear or branched ($C_1$–$C_6$)) alkyl, each alkyl portion being, independently of one another, identical or different, and R"b represents hydrogen or linear or branched ($C_1$–$C_6$) alkyl, its isomers as well as its addition salts with a pharmaceutically acceptable acid or base.

5. A compound of claim 1, in which R² and X, when X represents C—R³, form, together with the carbon atom which bears them, a ring of formula (II):

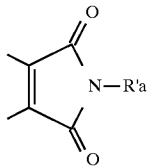

in which R'a represents (linear or branched ($C_1$–$C_6$) dialkyl) amino(linear or branched ($C_1$–$C_6$) alkyl), each alkyl portion being, independently of one another, identical or different, its isomers as well as its addition salts with a pharmaceutically-acceptable acid or base.

6. A compound of claim 5, in which R'a represents dimethylaminoethyl, its isomers as well as its addition salts with a pharmaceutically-acceptable acid or base.

7. A compound as claimed in claim 1 Which is N2-(7, 12-dioxa-3-hydroxybenzo[a]anthracene-5,6-maleimido)-N1,N1-dimethylethylenediamine or an addition salt thereof with a pharmaceutically acceptable acid or base.

8. A method for treating a cancer selected from the group consisting of murine leukemia, human epidermal carcinoma, and non-small-cell human pulmonary carcinoma in a living body in need thereof, comprising the step of administering to the living body an amount of a compound of claim 1, which is effective for alleviation of said cancer.

9. A pharmaceutical composition comprising as active principle an effective amount of a compound as claimed in claim 1, together with one or more pharmaceutically-acceptable excipients or vehicles.

10. A compound as claimed in claim 1 which is N2-(7, 12-dioxa-3-hydroxybenzo[a]anthracene-5,6-maleimido)-N1,N1-dimethylethylene-diamine hydrochloride.

* * * * *

UNITED STATES PATENT AND TRADEMARK OFFICE
CERTIFICATE OF CORRECTION

PATENT NO. : 5,807,882
DATED : Sep. 15, 1998
INVENTOR(S) : G. Coudert, S. Khatib, P. Moreau, D.H. Caignard, P. Renard, G. Atassi, A. Pierre It is certified that error appears in the above-identified patent and that said Letters Patent is hereby corrected as shown below:

Column 5, line 34: "n" at the beginning of the line, should read -- in --.

Column 12, line 5: "Stare A: should read -- Stage A --.

Column 12, line 52: "[SH]-" should read -- [5H] --.

Column 12, line 54: "3-[2-(t-butyloxycarbonylamion)" should read -- 3-[2-(t-butyloxycarbonylamino) --.

Column 14, line 58: "(IM)" should read -- 1M --.

Column 14, line 65: "Stave F:" should read: -- Stage F: --.

Column 15, line 1: "OC" should read -- 0°C --.

Column 15, line 35: "Stare A:" should read: -- Stage A: --.

Column 15, line 44: "OC" should read -- 0°C --.

Column 15, line 54: "Stare C: N2-" should read -- Stage C: $N^2$ --.

UNITED STATES PATENT AND TRADEMARK OFFICE
CERTIFICATE OF CORRECTION

PATENT NO. : 5,807,882
DATED : Sep. 15, 1998
INVENTOR(S) : G. Coudert, S. Khatib, P. Moreau, D.H. Caignard, P. Renard, G. Atassi, A. Pierre It is certified that error appears in the above-identified patent and that said Letters Patent is hereby corrected as shown below:

Column 17, line 6: At the beginning of the line, "$^6$-hydroxy-" should read -- 6-hydroxy- --.

Column 19, line 17: "Stake F: 7,1$^2$-" should read -- Stage F: 7,12- --.

Column 19, line 50: "The procedure is a s" should read -- The procedure is as --.

Column 19, line 58: "Stare A:" should read: -- Stage A: --.

Column 20, line 14: "1.2.4trihydro-7,12-" should read: -- 1,2,4-trihydro-7,12- --.

Column 21, line 41: "Stave A:" at the beginning of the line, should read: -- Stage A: --. Page 29, line 26

Column 22, line 2: "7.12 oxabenz[a]anthracene-6-[(1,3-hydroxy-3-" should read: -- 7,12-dioxabenz[a]anthracene-6-[(1,3-dihydroxy-3- --.

Column 22, line 9: "Stage B: 7,1$^2$-" at the beginning of the line, should read: -- Stage B: 7,12- --.

Column 22, line 21: "Delete "[" at the end of the line.

Column 22, line 22: Insert -- [ -- at the beginning of this line.

UNITED STATES PATENT AND TRADEMARK OFFICE
CERTIFICATE OF CORRECTION

PATENT NO. : 5,807,882
DATED : Sep. 15, 1998
INVENTOR(S) : G. Coudert, S. Khatib, P. Moreau, D.H. Caignard, P. Renard, G. Atassi, A. Pierre Page 3 of 4

It is certified that error appears in the above-identified patent and that said Letters Patent is hereby corrected as shown below:

Column 22, line 24: "Stare A:" should read:
-- Stage A: --.

Column 24, line 5: "KB-3°-1," should read -- KB-3-1, --.

Column 25, line 2: "maleimido)-n$^1$,n$^1$-dimethylethylene-"
should read -- maleimido)-N$^1$,N$^1$-dimethylethylene- --.
Page 35, line 5

Column 25, line 61: "CH, then R' and R$^2$" should read:
-- CH, then R$^1$ and R$^2$ --.

Column 26, line 8: "cally acceptable" should read
-- cally-acceptable --.

Column 26, line 14: "a pharmaceutically acceptable"
should read: -- a pharmaceutically-acceptable --.

Column 26, line 30: "pharmaceutically acceptable" should
read: -- pharmaceutically-acceptable --.

UNITED STATES PATENT AND TRADEMARK OFFICE
CERTIFICATE OF CORRECTION

PATENT NO. : 5,807,882
DATED : Sep. 15, 1998
INVENTOR(S) : G. Coudert, S. Khatib, P. Moreau, D.H. Caignard, P. Renard, G. Atassi, A. Pierre It is certified that error appears in the above-identified patent and that said Letters Patent is hereby corrected as shown below:

Column 26, line 52: "pharmaceutically acceptable" should read: -- pharmaceutically-acceptable --.

Signed and Sealed this

Second Day of March, 1999

Attest:

Q. TODD DICKINSON

*Attesting Officer*  *Acting Commissioner of Patents and Trademarks*